United States Patent [19]
Vogel et al.

[11] 3,937,730
[45] Feb. 10, 1976

[54] PLANT GROWTH REGULATING AGENT

[75] Inventors: Christian Vogel, Binningen; Rudolf Aebi, Basel, both of Switzerland

[73] Assignee: Ciba-Geigy Corporation, Ardsley, N.Y.

[22] Filed: Oct. 4, 1974

[21] Appl. No.: 511,321

Related U.S. Application Data

[63] Continuation-in-part of Ser. No. 366,955, June 4, 1973, abandoned.

[30] Foreign Application Priority Data

June 6, 1972 Switzerland............................ 08345
Mar. 30, 1973 Switzerland............................ 04607

[52] U.S. Cl................................. 260/562 B; 71/118
[51] Int. Cl.²....................................... C07C 103/34
[58] Field of Search..................... 260/562 B; 71/118

[56] References Cited
UNITED STATES PATENTS

| | | | |
|---|---|---|---|
| 3,547,620 | 12/1970 | Olin | 71/118 |
| 3,739,024 | 6/1973 | Chupp | 260/551 S |

*Primary Examiner*—C. Davis
*Attorney, Agent, or Firm*—Harry Falber; Karl F. Jorda

[57] ABSTRACT

2-ethyl-6-methyl-N-(1'-methoxyprop-2'-yl)-N-chloroacetanilide is disclosed as plant growth regulating and herbicidal agent with improved stability in the soil.

1 Claim, No Drawings

PLANT GROWTH REGULATING AGENT

CROSS-REFERENCE

This application is a continuation-in part of our application Ser. No. 366,955, filed June 4, 1973 and now abandoned.

The present invention relates to 2-ethyl-6-methyl-N(1'-methoxyprop-2'-yl)-N-chloroacetanilide having the formula I

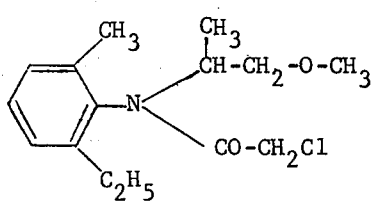

a process for its preparation as well as plant-growth regulating agents containing this compound as active ingredient and its use in the selective combatting of weeds in plant-cultures.

Various types of haloacetanilides have been described in the art as being herbicidally active.

In U.S. Pat. No. 3,442,945 it is stated that:

"It will be noted that the nitrogen-substituted α-haloacetanilides which are nuclear-substituted with a tertiary alkyl group in one ortho position and another substituent in the other ortho position possess unusual grass specifity and, furthermore, that these α-haloacetanilides have unusually high activity at extremely low application rates."

In accordance with this statement 2'-tert.butyl-2-chloro-N-ethoxyethyl-6'-ethylacetanilide of the formula A

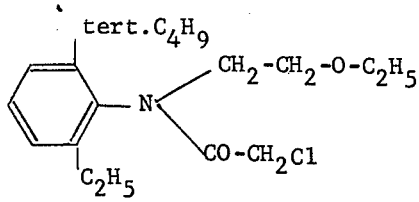

is highlighted inter alia as an example of a compound being especially active at low dosage levels. In example 85 of U.S. Patent No. 3,547,620 and appendant Table IV it is shown that 2-chloro-2'-tert.butyl-6'-ethyl-N-(ethoxymethyl)acetanilide of the formula A'

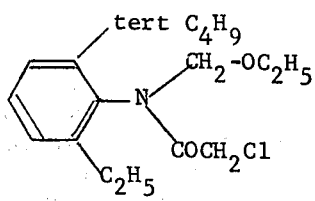

exhibits a 25 % improvement in herebicidal activity over that of the above compound A. Further herbicidal-test in tables V, VI and VII corroborate these findings and following conclusion is drawn:

"The difference in herbicidal effectiveness is directly related to the presence of an alkoxymethyl, instead of an alkoxyethyl or alkoxypropyl group, on the nitrogen atom of the acetanilide. It is immaterial, as is shown in this example, whether the halo is bromine or chlorine."

From the combined teachings of these patents it would follow that chloro- and bromoacetanilides containing an ethoxymethyl rather than an ethoxyethyl group on the nitrogen atom and particularily those with an ortho tert. butyl group are likely to possess the most favourable herbicidal activity for practicle purposes. However, the closest analog described in U.S. Pat. No. 3,547,620 is compound E shown hereinafter. Furthermore U.S. Pat. No. 3,739,024 shows that the conversion of haloacetanilides with thionophosphine sulfide produces Halothioacetanilides having particularily useful herbicidal properties. Halothioacetanilides containing the allegedly herbicidally less advantageous ethoxyethyl group at the nitrogen atom are exemplified.

Experience has now shown that in general the compounds described in the above references while possessing useful herbicidal properties lack sufficient stability in the ground. It is desirable that a selective herbicide used to protect a plant culture should possess not only an appropriate weedicidal spectrum but also a duration of activity such that one application per crop season will suffice to keep the treated locus weedfree through to harvest.

A broad-spectrum selective herbicide is of no real practical utility if it breaks down within 2 or 3 weeks of application thus requiring several applications per season with the concommitent increase in labour and costs.

A pre-emergent herbicide with sufficient in-soil durability avoids the necessity of further herbicides post-emergent application.

The ideal selective herbicide possesses an activity spectrum proper to the crop to be protected, a high weedicidal activity and a suitably long life after application. These criteria and desiderata apply equally to plant-growth regulating substances. All have to be taken into account when selecting a suitable herbicidal or plant-growth regulating agent.

It has now been found that the compound of the formula I in contrast to known acetanilide derivates fully satisfies all the above described requirements.

The active substance according to the invention possesses very good herbicidal activity against annual grasses such as Echinochloa and related plants of the genera Setaria, Digitaria, etc., against grasses such as Lolium species and against many dicotyledonous weeds such as Amaranthus, Stellaria, Chrysanthemum, Sinapis etc., without causing damage to the plant cultures in which it is intended to be used. Examples of such plants cultures are maize, sun flower, sugar beet, sugar cane, tobacco and potatoe, leguminous cultures such as soya, various types of ground nut (peanut), pea and various types of bean and also cotton and Brassica species such as rape and cabbage. The active substance may be applied either before or after germination of the plant culture and of the weeds or grasses (pre- and postemergent treatment). Suitable rates for pre-emergent application lie between 0.1 and 10 kg of active substance per hectare. At lower levels the compound acts selectively. For example with rates as low as and in the region of 2 kg/hectare weeds in a crop culture such as aforementioned are destroyed while the crop is left intact.

At higher rates the active substance acts as a total herbicide and may be employed for example to prevent railway embankments, factory areas, roads etc. from becomming overgrown.

When used for post-emergent treatment the compound acts as a plant-growth regulator in that it will delay or inhibit the growth of many mono- or di- cotyledonous plants be they plant cultures or weeds. Thus the growth rate of grassland (comprising for example Poa pratensis, Agrostis tenuis, Festuca rubra) treated with 5 kg/hectare of active substance shortly after the first cutting in spring is reduced by half an observation period of 60 days being used as a basis. The primary consequence of this activity is a reduction of the plant size in particular of its height. Accompanying changes in plantmorphology may be observed. As a direct result of the reduction in height the plant gains in sturdiness, the leaves and stems grow stronger and in the case of monocotyledones the reduction of the internodal distance results in greater resistance to bending and breaking. A further benefit of reduced growth in plant cultures and for example lawns, sports fields and other grassed-over areas is the saving in manure and/or fertilizer and in the case of the latter the reduced frequency at which they must be mown or scythed. A typical area of application would be to roadsides where the easy maintenance of medium growth-height throughout the vegetation period is desirable. The active substance of the formula I may of course be used in conjunction with other active substances. Additionally the compound I acts as an antisprouting agent on potatoes which are intended for storage or consumption. It also acts as fungicide to combat plantpathogenic fungi.

The compound of the formula I may be manufactured by reacting the N-substituted aniline of the formula II

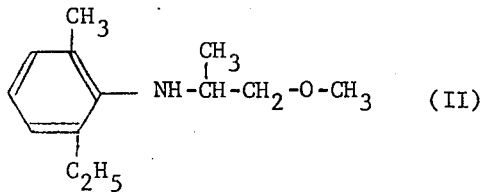

with a chloroacetylating agent, preferably an anhydride or halide of chloroacetic acid.

The compound of the formula I may also be produced by reacting 2-methyl-6-ethyl-aniline with a 2-halopropanol subsequently chloroacetylating the obtained compound of the formula IIa

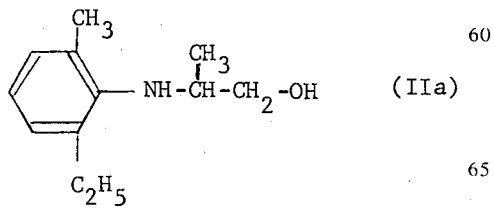

preferably with an anhydride or halide of chloroacetic acid and finally etherifying the free OH group with methanol in acid medium, (e.g. in the presence of HCl, $H_2SO_4$) under mild conditions and in a conventional manner.

The reactions can be carried out in the presence or absence of solvents or diluents which are inert towards the reactants. Examples of suitable solvents or diluents are:

aliphatic, aromatic or halogenated hydrocarbons, such as benzene, toluene, xylene, petroleum ether, chlorobenzene, methylene chloride, ethylene chloride, chloroform; ethers and ethereal compounds, such as dialkyl ethers, dioxan, tetrahydrofuran; nitriles, such as acetonitrile; N,N-dialkylated amides, such as dimethyl formamide; also dimethyl sulphoxide, as well as mixtures of these solvents.

Suitable chloroacetylating agents are for example chloroacetic anhydride, and chloroacetic halides, such as chloroacetyl chloride. However, it is also possible to carry out the reaction using chloroacetic acid, or its esters or amides. The reactions are carried out at temperatures between 0° and 200°C, preferably between 20° and 100°C. The chloroacetylation step is usefully carried out in the presence of an acid binding agent (especially if chloroacetyl halides are used). Suitable acid binding agents are: tertiary amines, such as trialkylamines, e.g. triethylamine, pyridine and pyridine bases, or inorganic bases, such as oxides and hydroxides, hydrogen carbonates and carbonates or alkali and alkaline earth metals. Furthermore, it is also possible to use an excess of the corresponding aniline of the formula II as acid binding agent.

Compounds homologous to formula II and hydroxyalkyl derivatives homologous to formula IIa are known, e.g. from U.S. Pat. No. 2.381.071, 2.759.943 as well as from Am. Soc. 84, 743 and Bull. Soc. Chim. France 1962, 303 and 1965, 2037.

The starting material of the formula II may be manufactured for example by one of the following known methods:

a. condensation of 2-methyl-6-ethyl-aniline with methoxyacetone and simultaneous or subsequent catalytic hydrogenation of the resulting azomethine of the formula III

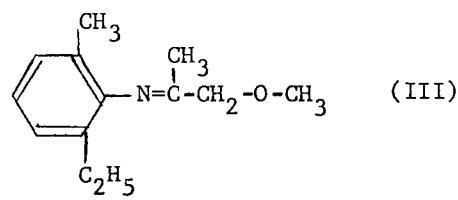

or b. reaction of 2-methyl-6-ethyl-aniline with a compound of the formula IV

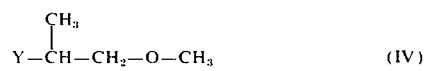

wherein Y represents a halogen atom or another anionic group in particular an arylsulphonate radical. Compounds of the formula IV with a benzenesulphonate acid radical as Y are described e.g. in Can. J. Chem. 33, 1207, and those with a tosyloxy radical ($CH_3$—$C_6$-

$H_4$—$SO_3$—) in British patent 869,083. There are, of course, a number of other processes for the manufacture of the starting materials of the formula II from ortho-alkylated anilines.

The following Examples illustrates the invention:

EXAMPLE 1 a. A mixture of 540 g (4.0 moles) of 2-ethyl-6-methylaniline and 306 g (2.0 moles) of 2-bromo-1-methoxypropane is heated for 40 hours at reduced pressure (10 mm Hg) to 120°C with stirring. After it has cooled, the light red, viscous solution is diluted with 200 ml of water and made alkaline with 210 ml of conc. sodium hydroxide solution. The precipitated product is taken up in ether, and the ethereal solution is washed neutral with water, dried, and evaporated.

Distillation of the residue yields pure 2-ethyl-6-methyl-N-[1'-methoxy-prop-2'-yl]-aniline which boils at 64°–66°C/0.07 Torr.

b. A solution of 9.7 g (0.047 mole) of the intermediate described under a) and 5.05 g (0.05 mole) of triethylamine in 30 ml of benzene is treated dropwise with a solution of 5.65 g (0.05 mole) of chloroacetyl chloride in 10 ml of absolute benzene, and the mixture is further stirred for 2 hours at room temperature. The reaction mixture is diluted with ether, the solution repeatedly washed with water, and dried. The solvent mixture is evaporated off in vacuo to give pure 2-ethyl-6-methyl-N-[1'-methoxy-prop-2'-yl]-chloroacetanilide, $n_D^{20}$: 1.5301.

Analysis: calculated: C 63.5 H 7.8 N 4.9%. found: C 63.7 H 8.1 N 5.0%. The compound of the formula I exhibits a clear superiority over compounds which are structurally or otherwise related and which are said to have a good herbicidal properties.

Comparative Compounds

A 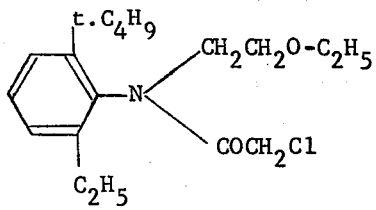 (Compd. No 72 in Table IV of USP. 3,442,945)

B 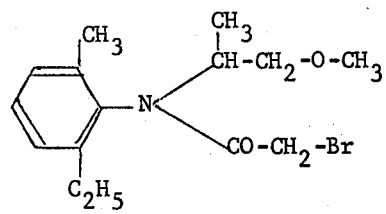 (previously unknown)

C 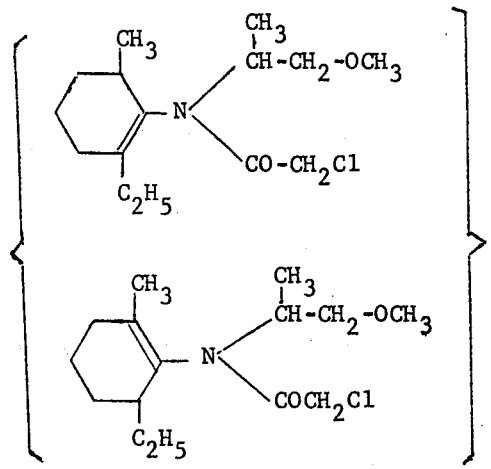 (from the scope of USP 3,586,496)

As has already been outlined in the introductory part of this specification comparative compound A belongs to a group which is said to have unusually high activity at extremely low application rates.

Comparative compound B is included to verify the claim made at lines 5 to 10 in column 14 of U.S. Pat. No. 3,547,620 that for effectiveness it is immaterial whether the haloacetyl is chloroacetyl or bromoacetyl. "Compound C" is a mixture of the two isomers shown above which are enamines.

Although the formal representation of these isomers suuggests a close similarity between them and the compound of the invention, this is chemically not the case (cf. A. G. Cook, Ed. Marcel Dekker Ltd., New York and London, 1969). A description of a process for the preparation of the hitherto undescribed compound C follows.

Preparation of comparative substance C i. Starting material 163 g of titanium tetrachloride in 800 ml of toluene were added dropwise to a solution of 229 g (1,64 mole) of 2-ethyl-6-methyl-cyclohexanon and 435 g (4,9 mole) of 1-methyl-2-methoxy-ethylamine in 1000 ml toluene and 110 ml of ether over a period of two hours with stirring and at a temperature of between 0°–10°C. After distilling off the ether the reaction mixture was refluxed for 6½ hours. After cooling the precipitate was filtered off and the filtrate concentrated in a rotary evaporator at 50°C. Distillation of the residue under reduced pressure gave 174 g 2-ethyl-6-methyl-N-(1-methyl-2-methoxy-ethyl)-cyclohexylidene-amine, m.p. 109°–113°C/15 Torr.

ii. End compound 174 g (0,83 mole) of 2-ethyl-6-methyl-N-(1-methyl-2-methoxy-ethyl)-cyclohexylideneamine and 101 g (1 mole) of triethylamine were added dropwise one after the other with stirring and at a temperature of 5°C to a solution of 94 g (0,83 mole) of chloroacetyl chloride in 3000 ml of benzene. The reaction mixture was then refluxed for 5 hours, cooled to room temperature, washed with water, dried with sodium sulfate, filtered and concentrated under water-jet vacuum. Distillation of the residue under high vacuum gave 150,5 g of a 2-chloro-N-(1-methyl-2-methoxy-ethyl)N-(2-ethyl-6-methyl-cyclohexenyl)acetamide as a mixture of its isomers b.p. 140°–148°/0.1 Torr.

| | C | H | Cl | N |
|---|---|---|---|---|
| $C_{15}H_{26}ClNO_2$ Calculated | 62,59 | 9,11 | 12,32 | 4,86 % |
| Found | 62,7 | 9,4 | 12,2 | 5,0 % |

2-Ethyl-6-methyl-N-(1'-methoxyprop-2'-yl)-N-chloroacetanilide of the formula I is markedly superior to the structurally most closest known comparative compounds listed below in respect of all significant criteria for a selective herbicide to wit activity, selectivity and stability as well with regard to its growth inhibiting properties on post-emergent grass.

Comparative Compounds

D 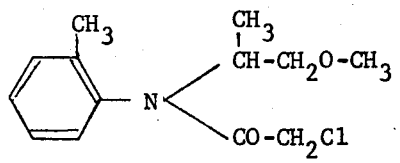

(disclosed in German Offenlegungsschrift No. 1'903'198)

E 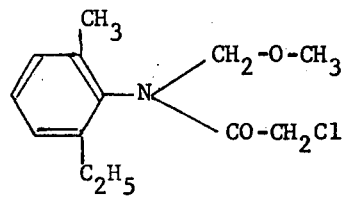

(No. 54 in USP. 3'547'620)

F 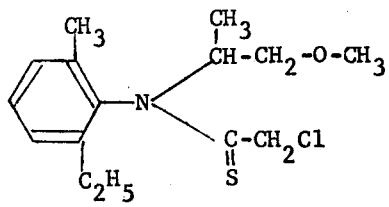

(according to USP. 3'739'024)

EXAMPLE 2

Combating of weeds in various cultures of useful plants (preemergence method)

One day after the test plants have been sown in seed dishes (9.6 cm height, 11 cm diameter at the top), dilute aqueous suspensions of the active substances are sprayed in such concentrations on the surface of the soil as to correspond to rates of application of 2 kg, 1 kg, 0.5 kg and 0.25 kg per hectare. The seed dishes are kept at 19° to 21°C and 50–60% relative humidity. The test is evaluated after 26 days according to the following rating:

9 = plants undamaged (as control test)
1 = plants destroyed
8–2 = intermediate stages of damage
— = not tested The following weeds were employed in the tests.
Ipo = Ipomoea = Morning glory Sin = Sinapis = Mustard
Ama = Amaranthus = Pigweed
Ses = Sesbania = Coffeeweed
Dat = Datura = Jimsonweed
Koch = Kochia = Kochia
Abu = Abutilon = Velvet leaf
Stell = Stellaria = Chickweed; Side = Teaweed
Chrys = *Chrysanthemum* segetum = Corn marigold
Avena = Avenafatua = Wild oat
Alo = Alopecurus = Black grass; Poa = Annual meadow grass
Fes = Festuca = Fescue
Sorg. alm= *Sorghum almum* = Sorghum almum
Pha = Phalaris = Canary grass
Sorg. hal= *Sorghum halepense* = Johnsongrass
Dig = Digitaria = Crabgrass
Pani = *Panicum ramosum* = Wild millet
Rott = Rottboellia = Raoul grass
Set = *Setaria italica* = Italian foxtail
Ech = *Echinochloa crus-galli* = Barnyard grass The results are shown in the following 4 Tables:

a) Application rate: 2 kg/hectare

| Plant \ Compd. | I | A | B | C | D | E | F |
|---|---|---|---|---|---|---|---|
| Corn | 7 | 9 | 9 | 3 | 8 | 6 | 9 |
| Soy beans | 7 | 9 | 7 | 9 | 9 | 4 | 9 |
| Beans (Phaseolus) | 9 | 9 | 8 | 9 | 9 | 6 | 9 |
| Ipo | 7 | 9 | 9 | 9 | 5 | 7 | 9 |
| Sin | 4 | 9 | 9 | 9 | 6 | 5 | 9 |
| Ama | 1 | 6 | 7 | 3 | 1 | 1 | 1 |
| Ses | 5 | 9 | 9 | 9 | 6 | 3 | 9 |
| Dat | 4 | 9 | 9 | 8 | 4 | 4 | 7 |
| Koch | 7 | 9 | 9 | 9 | 6 | 1 | 9 |
| Abu | 8 | 9 | 9 | 8 | 9 | 4 | 8 |
| Stell | 1 | 9 | 9 | 7 | 3 | 1 | 5 |
| Sida | 4 | 9 | 8 | 9 | 3 | 2 | 9 |
| Chrys | 3 | 9 | 9 | 8 | 3 | 2 | 9 |
| Avena | 2 | 9 | 8 | 4 | 4 | 1 | 9 |
| Alo | 2 | 9 | 3 | 1 | 2 | 1 | 6 |
| Poa | 2 | 9 | 3 | 1 | 1 | 1 | 3 |
| Fes | 1 | 9 | 1 | 1 | 1 | 1 | 1 |
| Sorg.alm. | 2 | 9 | 1 | 2 | 2 | 1 | 2 |
| Pha | 1 | 9 | 1 | 1 | 1 | 1 | 6 |
| Sorg.hal. | 1 | 9 | 2 | 1 | 1 | 1 | 4 |
| Dig | 1 | 8 | 2 | 1 | 1 | 1 | 1 |
| Pani | 1 | 9 | 1 | 1 | 1 | 1 | 2 |
| Rott | 2 | 9 | 8 | 7 | 7 | 3 | 9 |
| Set | 1 | 9 | 2 | 1 | 1 | 1 | 1 |
| Ech | 1 | 9 | 1 | 1 | 1 | 1 | 1 | b) Application rate 1kg/hectare

| Plant \ Compd. | I | A | B | C | D | E | F |
|---|---|---|---|---|---|---|---|
| Corn | 7 | 9 | 9 | 4 | 9 | 8 | 9 |
| Soybeans | 8 | 9 | 8 | 9 | 9 | 4 | 9 |
| Beans (Phaseolus) | 9 | 9 | 8 | 9 | 9 | 6 | 9 |
| Ipo | 9 | 9 | 9 | 9 | 7 | 9 | 9 |
| Sin | 6 | 9 | 9 | 9 | 8 | 6 | 9 |
| Ama | 1 | 9 | 7 | 5 | 1 | 1 | 3 |
| Ses | 6 | 9 | 9 | 9 | 7 | 3 | 9 |
| Dat | 4 | 9 | 9 | 9 | 4 | 4 | 7 |
| Koch | 9 | 9 | 9 | 9 | 6 | 1 | 9 |
| Abu | 8 | 9 | 9 | 9 | — | 4 | 9 |
| Stell | 2 | 9 | 9 | 9 | 5 | 2 | 6 |
| Sida | 4 | 9 | 9 | 9 | 4 | 3 | 9 |
| Chrys | 3 | 9 | 9 | 9 | 5 | 3 | 9 |
| Avena | 5 | 9 | 8 | 7 | 4 | 2 | 9 |
| Alo | 2 | 9 | 6 | 3 | 3 | 3 | 9 |
| Poa | 2 | 9 | 5 | 3 | 1 | 1 | 4 |
| Fes | 1 | 9 | 2 | 1 | 1 | 1 | 2 |
| Sorg.alm | 1 | 9 | 2 | 2 | 6 | 2 | 2 |
| Pha | 1 | 9 | 3 | 1 | 3 | 1 | 6 |
| Sorg.hal | 2 | 9 | 2 | 1 | 6 | 1 | 7 |
| Dig | 1 | 9 | 3 | 1 | 1 | 1 | 1 |
| Pani | 1 | 9 | 1 | 1 | 1 | 1 | 2 |
| Rott | 2 | 9 | 8 | 7 | 9 | 3 | 9 |
| Set | 1 | 9 | 5 | 2 | 1 | 1 | 2 |
| Ech | 1 | 9 | 2 | 1 | 1 | 1 | 2 | c) Application rate 0.5 kg/hectare

| Plant \ Compd. | I | A | B | C | D | E | F |
|---|---|---|---|---|---|---|---|
| Corn | 9 | 9 | 9 | 7 | 9 | 9 | 9 |
| Soybeans | 9 | 9 | 8 | 9 | 9 | 7 | 9 |
| Beans (Phaseolus) | 9 | 9 | 9 | 9 | 9 | 8 | 9 |
| Ipo | 9 | 9 | 9 | 9 | 7 | 9 | 9 |
| Sin | 8 | 9 | 9 | 9 | 8 | 8 | 9 |
| Ama | 1 | 9 | 8 | 8 | 1 | 1 | 4 |
| Ses | 9 | 9 | 9 | 9 | 8 | 7 | 9 |
| Dat | 5 | 9 | 9 | 9 | 6 | 7 | 9 |
| Koch | 9 | 9 | 9 | 9 | 7 | 2 | 9 |
| Abu | 8 | 9 | 9 | 9 | 9 | 7 | 9 |
| Stell | 2 | 9 | 9 | 9 | 6 | 2 | 8 |
| Sida | 7 | 9 | 9 | 9 | 4 | 5 | 9 |
| Chrys | 8 | 9 | 9 | 5 | 5 | 6 | 9 |
| Avena | 6 | 9 | 9 | 9 | 6 | 5 | 9 |
| Alo | 4 | 9 | 9 | 7 | 4 | 3 | 9 |
| Poa | 3 | 9 | 8 | 6 | 1 | 1 | 6 |
| Fes | 1 | 9 | 3 | 1 | 1 | 1 | 2 |
| Sorg.alm | 2 | 9 | 6 | 2 | 6 | 2 | 7 |
| Pha | 2 | 9 | 7 | 1 | 4 | 1 | 7 |
| Sorg.hal | 2 | 9 | 6 | 1 | 6 | 1 | 8 |
| Dig | 1 | 9 | 4 | 1 | 1 | 1 | 1 |
| Pani | 1 | 9 | 2 | 1 | 1 | 1 | 7 |
| Rott | 7 | 9 | 9 | 9 | 9 | 6 | 9 |
| Set | 1 | 9 | 5 | 2 | 1 | 1 | 3 |
| Ech | 1 | 9 | 2 | 2 | 1 | 1 | 3 | d) Application rate 0.25 kg/hectare

| Plant \ Compd. | I | A | B | C | D | E | F |
|---|---|---|---|---|---|---|---|
| Corn | 9 | 9 | 9 | 8 | 9 | 9 | 9 |
| Soybeans | 9 | 9 | 9 | 9 | 9 | 8 | 9 |
| Beans (Phaseolus) | 9 | 9 | 9 | 9 | 9 | 9 | 9 |
| Ipo | 9 | 9 | 9 | 9 | 8 | 9 | 9 |
| Sin | 8 | 9 | 9 | 9 | 8 | 9 | 9 |
| Ama | 1 | 9 | 9 | 9 | 1 | 1 | 5 |
| Ses | 9 | 9 | 9 | 9 | 8 | 9 | 9 |
| Dat | 5 | 9 | 9 | 9 | 6 | 9 | 9 |
| Koch | 9 | 9 | 9 | 9 | 8 | 5 | 9 |
| Abu | 8 | 9 | 9 | 9 | 9 | 7 | 9 |
| Stell | 4 | 9 | 9 | 9 | 8 | 3 | 9 |
| Sida | 8 | 9 | 9 | 9 | 7 | 7 | 9 |
| Chrys | 9 | 9 | 9 | 9 | 7 | 7 | 9 |
| Avena | 7 | 9 | 9 | 9 | 8 | 5 | 9 |
| Alo | 6 | 9 | 9 | 9 | 6 | 4 | 9 |
| Poa | 3 | 9 | 9 | 9 | 3 | 1 | 7 |
| Fes | 1 | 9 | 4 | 3 | 1 | 1 | 2 |
| Sorg.alm | 2 | 9 | 7 | 2 | 6 | 2 | 9 |
| Pha | 2 | 9 | 7 | 2 | 5 | 1 | 9 |
| Sorg.hal | 2 | 9 | 8 | 1 | 6 | 1 | 9 |
| Dig. | 1 | 9 | 6 | 1 | 1 | 1 | 3 |
| Pani | 1 | 9 | 3 | 4 | 1 | 1 | 8 |
| Rott | 8 | 9 | 9 | 9 | 9 | 8 | 9 |
| Set | 1 | 9 | 7 | 2 | 1 | 1 | 5 |
| Ech | 1 | 9 | 4 | 3 | 1 | 1 | 3 |

EXAMPLE 3

The following tests compare the compound of the invention with comparative compounds D, E and F with respect to in-soil stability on pre-emergent application.

Arable soil comprising ca.4% organic substance, 21% clay, 32% silt and 43% sand and contained in a plastic basin (50 cm × 32 cm × 7 cm) was sprayed with test-substance in the form of a broth prepared from an emulsion concentrate to give an active substance concentration equivalent to 2, 1 and 0.5 kg/hectare. Two parallel rows of weeds were sown in each basin and a further two rows were sown weekly over the next 6 weeks. Setaria italica was chosen as test weed since it is especially sensitive to compounds of type under test.

The condition of the weeds in each set of two rows was evaluated 3 weeks after sowing. The test conditions were: temp. 19°–23°C; rel. humidity 50°–60%; watering - normal.

Key as in example 2.

a) Application rate: 2 kg/hectare

| Compd. | Weeks 0 | 1 | 2 | 3 | 4 | 5 | 6 |
|---|---|---|---|---|---|---|---|
| I | 1 | 1 | 1 | 1 | 2 | 1 | 2 |
| C | 1 | 1 | 1 | 1 | 3 | 4 | 6 |
| D | 1 | 1 | 1 | 2 | 3 | 5 | 9 |
| E | 1 | 1 | 2 | 5 | 9 | 9 | 9 |
| F | 2 | 1 | 3 | 4 | 5 | 5 | 6 | b) Application rate: 1 kg/hectare

| Compd. | Weeks 0 | 1 | 2 | 3 | 4 | 5 | 6 |
|---|---|---|---|---|---|---|---|
| I | | 1 | 1 | 3 | 3 | 3 | 2 | 4 |
| C | | 1 | 1 | 4 | 4 | 6 | 8 | 9 |
| D | | 2 | 2 | 2 | 4 | 4 | 9 | 9 |
| E | | 1 | 2 | 8 | 9 | 9 | 9 | 9 |
| F | | 2 | 3 | 4 | 5 | 5 | 8 | 9 | c) Application rate: 0.5 kg/hectare

| Compd | Weeks 0 | 1 | 2 | 3 | 4 | 5 | 6 |
|---|---|---|---|---|---|---|---|
| I | 2 | 2 | 4 | 4 | 4 | 4 | 8 |
| C | 2 | 2 | 5 | 6 | 8 | 9 | 9 |
| D | 2 | 5 | 8 | 8 | 9 | 9 | 9 |
| E | 1 | 5 | 6 | 9 | 9 | 9 | 9 |
| F | 4 | 4 | 8 | 9 | 9 | 9 | 9 |

EXAMPLE 4

Growth inhibition in grasses (postemergence method)

Seeds of the grasses Lolium perenne, Poa pratensis, Festuca ovina, and Dactylis glomerata were sown in plastic dishes filled with an earth/turf/sand mixture. After 3 weeks the germinated grasses were cut back to a height of 4 cm above the soil and 2 days later sprayed with aqueous spray broths of active substances of the formula I. The amount of active substance corresponded to a rate of application of 5 kg of active substance per hectare. 21 days after application the growth of the grasses was evaluated according to the following linear rating:

1 = strong inhibition (no growth from the time of application)

9 = no inhibition (growth as untreated control)

The following results were obtained:

| Compound | Lolium perenne | Poa pratensis | Festuca ovina | Dactylis glomerata |
|---|---|---|---|---|
| I | 2 | 3 | 1 | 6 |
| C | 7 | 9 | 9 | 9 |
| D | 4 | 3 | 3 | 3 |
| E | 7 | 6 | 7 | 8 |
| F | 7 | 6 | 6 | 9 |

None of the comparative compounds C, E and F has useful growth retarding properties. Only compound D has an activity equivalent to that of compound I. However, the fast degradation of compound D in the soil makes it unsuitable for practical use.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
dusts, tracking agents, granules, coated granules, impregnated granules and homogeneous granules.

Liquid forms:
a. active substances which are dispersible in water: wettable powders, pastes, emulsions;
b. solutions.

To manufacture solide forms (dusts, tracking agents), the active substances are mixed with solid carriers. Suitable carriers are, for example: kaolin, talcum, bolus, loess, chalk, limestone, ground limestone, attaclay, dolomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.1% to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products. Preferred dispersions (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of oleoyl methyl tauride, ditertiary acetalene glycols, dialkyl dilauryl ammonium chloride and fatty acid alkali and alkaline earth metal salts.

Suitable anti-foam agents are silicones. The active substance is so mixed, groud sieved and strained with the additives mentioned above that, in wettable powders, the solid particle size of from 0.02 to 0.04 and in pastes, of 0.03 is not exeeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulphoxide, N.N-dialkylated amides, N-oxides of amines (whereas N-oxides of trialkylamines are preferred), and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substance or several active substances of general formula I are dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1 to 20%.

The agents described according to the invention can be mixed with other biocidally active substances or agents. Thus in order to broaden the activity spectrum the new agents may contain, for example, insecticides, fungicides, bactericides, fungistatics, bacteriostatics, nematocides or further herbicides, in addition to the cited active substances of the formula I. The agents according to the invention may also contain plant fertilisers, trace elements etc.

The active substances of the formula I can, for example, be formulated as follows. The parts denote parts by weight.

Granules

The following substances are used to manufacture 5% granules:

5 parts of 2-Ethyl-6-methyl-N-(1'-methoxyprop-2'-yl)-N-chloroacetanilide,
0.25 parts of epichlorohydrin,
0.25 parts of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable powder

The following constituents are used to manufacture (a) a 50%, (b) a 25% and (c) a 10% wettable powder:

a.
  50 parts of 2-Ethyl-6-methyl-N-(1'-methoxyprop-2'-yl)-N-chloroacetanilide,
  5 parts of sodium dibutylnaphthalene sulphonate,
  3 parts of naphthalenesulphonic acid/phenolsulphonic acid/formaldehyde condensate (3:2:1),
  20 parts of kaolin,
  22 parts of Champagne chalk;
b.
  25 parts of 2-Ethyl-6-methyl-N-(1'-methoxyprop-2'-yl)-N-chloroacetanilide,
  5 parts of oleylmethyltaurid-sodium-salt,
  2.5 parts of naphthalenesulphonic acid/formaldehyde condensate,
  0.5 part of carboxymethyl cellulose,
  5 parts of neutral potassium-aluminium-silicate,
  62 parts of kaolin;
c.
  10 parts of compound I
  3 parts of a mixture of the sodium salts of saturated fatty alcohol sulphates,
  5 parts of naphthalenesulphonic acid/formaldehyde condensate,
  82 parts of kaolin.

The indicated active substance is applied to the corresponding carriers (kaolin and chalk and then these are mixed and ground, to yield wettable powders of excellent wettability and having an excellent capacity for forming suspensions. By diluting these wettable powders with the 10-fold amount of water it is possible to obtain suspensions of any desired concentration.

Paste

The following substances are used to manufacture a 45% paste:

45 parts of compound I
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of every desired concentration of active substance.

Emulsion Concentrate

To manufacture a 25% emulsion concentrate
25 parts of compound I 5 parts of a mixture of nonylphenolpolyoxy-ethoxyethylene and calcium dodecylenesulphonate,
35 parts of 3,5,5-trimethyl-2-cyclohexan-1-one,
35 parts of dimethyl formamide,
are mixed together. This concentrate can be diluted with water to give emulsions in desired concentrations. Such emulsions are suitable for combating weeds in cultures of crop plants.

What we claim is:
1. The compound 2-ethyl-6-methyl-N-(1'-methoxyprop-2'-yl)-N-chloroacetanilide of the formula

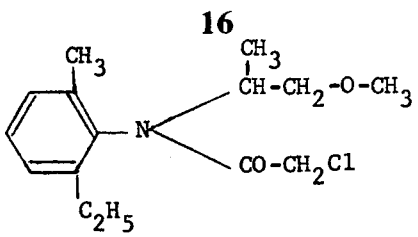

* * * * *